| (12) | United States Patent | (10) Patent No.: | US 11,235,314 B2 |
|---|---|---|---|
| | Li et al. | (45) Date of Patent: | Feb. 1, 2022 |

(54) CATALYST FOR CATALYTIC OXIDATION OF FURFURAL TO PREPARE MALEIC ACID AND APPLICATION THEREOF

(71) Applicant: HEFEI ENERGY RESEARCH INSTITUTE, Hefei (CN)

(72) Inventors: Wenzhi Li, Hefei (CN); Tao Yang, Hefei (CN); Mingxue Su, Hefei (CN); Jianru Ma, Hefei (CN)

(73) Assignee: HEFEI ENERGY RESEARCH INSTITUTE, Hefei (CN)

( * ) Notice: Subject to any disclaimer, the term of this patent is extended or adjusted under 35 U.S.C. 154(b) by 10 days.

(21) Appl. No.: 16/613,810

(22) PCT Filed: Jan. 30, 2019

(86) PCT No.: PCT/CN2019/074022
§ 371 (c)(1),
(2) Date: Nov. 15, 2019

(87) PCT Pub. No.: WO2020/098161
PCT Pub. Date: May 22, 2020

(65) Prior Publication Data
US 2021/0154647 A1    May 27, 2021

(30) Foreign Application Priority Data
Nov. 16, 2018    (CN) .......................... 201811367627.5

(51) Int. Cl.
| C07C 51/31 | (2006.01) |
| B01J 27/08 | (2006.01) |
| B01J 23/04 | (2006.01) |

(52) U.S. Cl.
CPC ............... *B01J 27/08* (2013.01); *B01J 23/04* (2013.01); *C07C 51/31* (2013.01); *C07C 51/313* (2013.01)

(58) Field of Classification Search
CPC ..................................................... C07C 51/23
See application file for complete search history.

(56) References Cited

U.S. PATENT DOCUMENTS

| 5,246,903 A | 9/1993 | Harley |
| 2019/0091676 A1 | 3/2019 | Wang et al. |

FOREIGN PATENT DOCUMENTS

| CN | 103910699 A | 7/2014 |
| CN | 105130783 A | 12/2015 |
| CN | 106925349 A | 7/2017 |
| WO | 2018171251 A1 | 9/2018 |

OTHER PUBLICATIONS

Xiang et al. Catalysis Communications 86 (2016) 41-45.*
Moriyama et al. J. Org. Chem. 2014, 79, 6094-6104.*

* cited by examiner

*Primary Examiner* — Ana Z Muresan
(74) *Attorney, Agent, or Firm* — Bayramoglu Law Offices LLC

(57) ABSTRACT

A catalyst for catalytic oxidation of furfural to prepare maleic acid, relating to the technical field of renewable energy. The catalyst is a mixture of a bromide and a base. A method for preparing the catalyst in catalytic oxidation of furfural to prepare maleic acid. The method includes: mixing the furfural, the bromide-base, an oxidant and a solvent to carry out a reaction to obtain the maleic acid. The present invention has the advantages that the method has a relatively high conversion rate of furfural and a relatively high yield of maleic acid, the conversion rate of furfural is up to 99%, the yield of maleic acid is up to 68.04%; and the catalyst has a high catalytic selectivity and reusability.

7 Claims, 2 Drawing Sheets

CATALYST FOR CATALYTIC OXIDATION OF FURFURAL TO PREPARE MALEIC ACID AND APPLICATION THEREOF

CROSS REFERENCE TO THE RELATED APPLICATIONS

This application is the national phase entry of International Application No. PCT/CN2019/074022, filed on Jan. 30, 2019, which is based upon and claims priority to Chinese Patent Application No. 201811367627.5, filed on Nov. 16, 2018, the entire contents of which are incorporated herein by reference.

TECHNICAL FIELD

The present disclosure relates to the technical field of renewable energy, and more specifically to a catalyst for catalytic oxidation of furfural to prepare maleic acid and an application thereof.

BACKGROUND

Maleic acid, as an important chemical raw material and intermediate, is widely used in industry. Maleic acid is mainly used to manufacture unsaturated polyester resin, and may also be used as a novel acidulant in the food and beverage industry. By adding an appropriate amount of maleic acid, a special fruit flavor can be enhanced and the taste can be improved. Currently, approximately 1.8 million tons of maleic acid is required worldwide every year. Therefore, efficient production of maleic acid especially using renewable resources to produce maleic acid is an important matter.

There are many methods for producing maleic acid. The main method used in the industry is to oxidize benzene with air at 450-500° C. under the catalytic condition of using vanadium pentoxide as a catalyst, where maleic anhydride is first generated and then hydrolyzed to obtain the maleic acid. This method has disadvantages of using fossil fuels, and the reaction condition is extremely strict that the reaction has to be performed at a high temperature and high pressure.

At present, the technique of using renewable carbon sources to replace fossil fuels for producing maleic acid has attracted great attention both at home and abroad, and has also achieved a rapid progress. However, while producing maleic acid from renewable carbon resources, problems such as low conversion rate of raw materials and low product yield exist.

SUMMARY

The present invention aims to solve the problems associated with producing maleic acid by using fossil fuels as raw materials, by utilizing strict reaction conditions, by having low conversion rate of raw materials, and having low yield of maleic acid in the methods used for preparing maleic acid in the prior art.

The present invention solves the above technical problems by the following technical solutions.

The present invention provides a catalyst for catalytic oxidation of furfural to prepare maleic acid, where the catalyst is a bromide-base, and the bromide-base is a mixture of a bromide and a base.

Preferably, the base is a metal hydroxide or a metal oxide.

Preferably, the bromide is potassium bromide or sodium bromide.

The present invention further provides an application of the above catalyst in catalytic oxidation of furfural to prepare maleic acid. The preparation method includes: mixing the furfural, the bromide-base, an oxidant and a solvent to carry out a reaction to obtain the maleic acid.

Preferably, a mass ratio of the furfural to the bromide-base is (1-1000):100.

Preferably, the oxidant is one or more selected from the group consisting of hydrogen peroxide, potassium permanganate, potassium chlorate and oxygen.

Preferably, an amount of the oxidant in a mixed system composed of the furfural, the bromide-base, the oxidant and the solvent is 1-1000 mmol/L.

Preferably, the solvent is water.

Preferably, the reaction is carried out at 30-120° C. for a reaction time of 0.5-12 h.

Preferably, the reaction is carried out under a stirring condition at a stirring rate ranging from 200 to 1000 rpm.

The advantages of the present invention are as follows.

(1) In the preparation method provided by the present invention, the maleic acid is obtained by using furfural as a reaction raw material under the condition of potassium bromide-base catalysis, thereby avoiding the use of fossil fuel products such as benzene and butene, which is beneficial to the sustainable development of environmental resources;

(2) By using the catalyst and the preparation method of the present invention for catalytic oxidation of furfural to prepare maleic acid, a relatively high conversion rate of furfural and a relatively high yield of maleic acid are achieved. The conversion rate of furfural is more than 99%, and the yield of maleic acid is up to 68.04%.

(3) The bromide-base catalyst used in the present invention is easily available, and has a high catalytic selectivity and reusability.

DETAILED DESCRIPTION OF THE EMBODIMENTS

The present invention is further described in detail below with reference to the drawings and embodiments of the specification.

The test materials, reagents, etc. used in the following embodiments are commercially available unless otherwise specified.

Embodiment 1

Maleic acid was prepared by catalytic oxidation of furfural with potassium bromide-potassium hydroxide as a catalyst. The preparation method includes the following steps:

1 mmol of furfural, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected, and the results showed that the main component of the filtrate was maleic acid with a yield of 68.04%.

Figure 1:
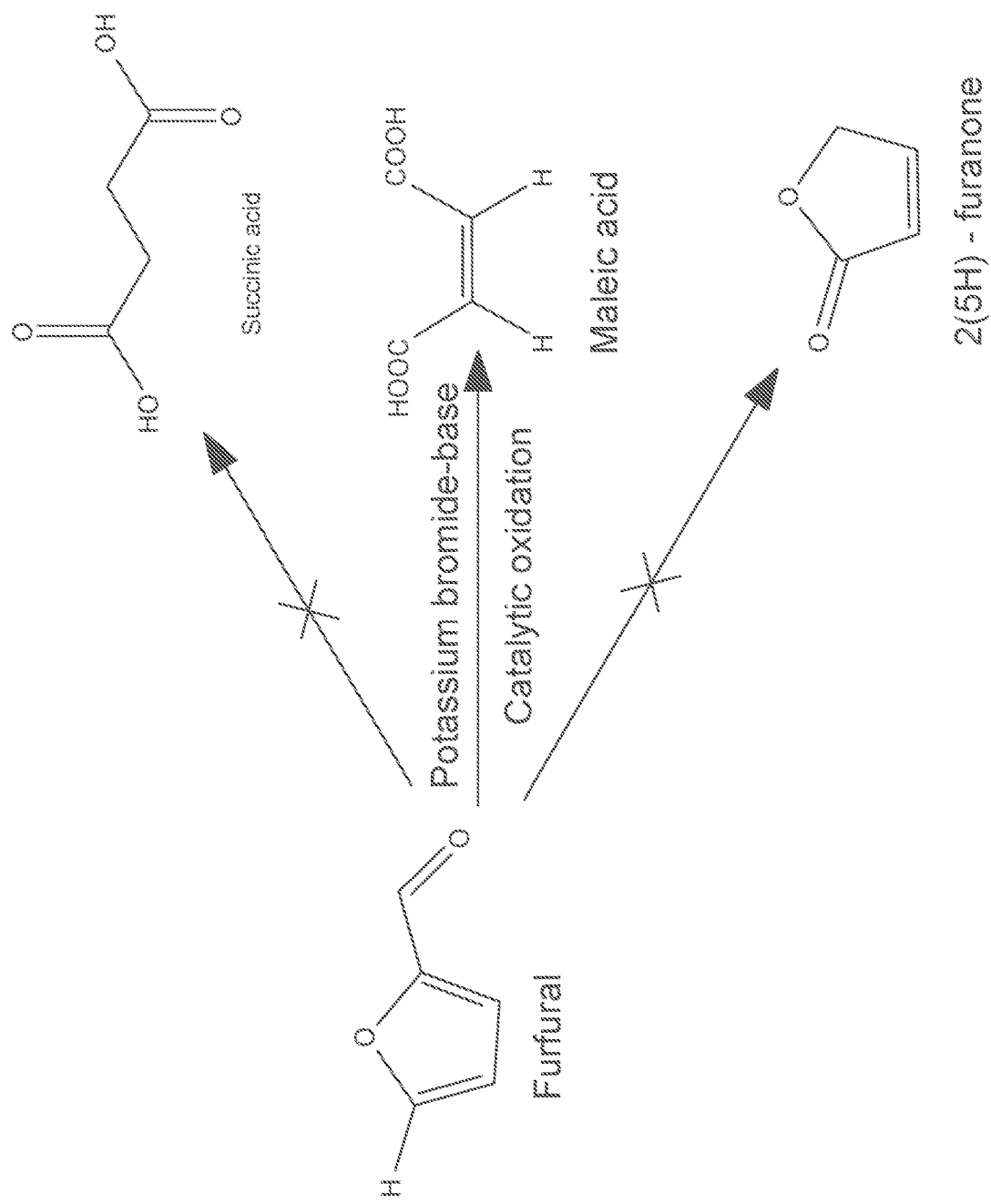
FIG. 1 is a diagram showing a product distribution of furfural under a catalytic oxidation of potassium bromide-base.

The filtrate was diluted 20 times, and then measured and analyzed by using Waters 515 HPLC (high performance liquid chromatography). The result showed that the conversion rate of furfural was more than 99%. FIG. 1 shows the product distribution of furfural under the catalytic oxidation of potassium bromide-base.

Figure 2:
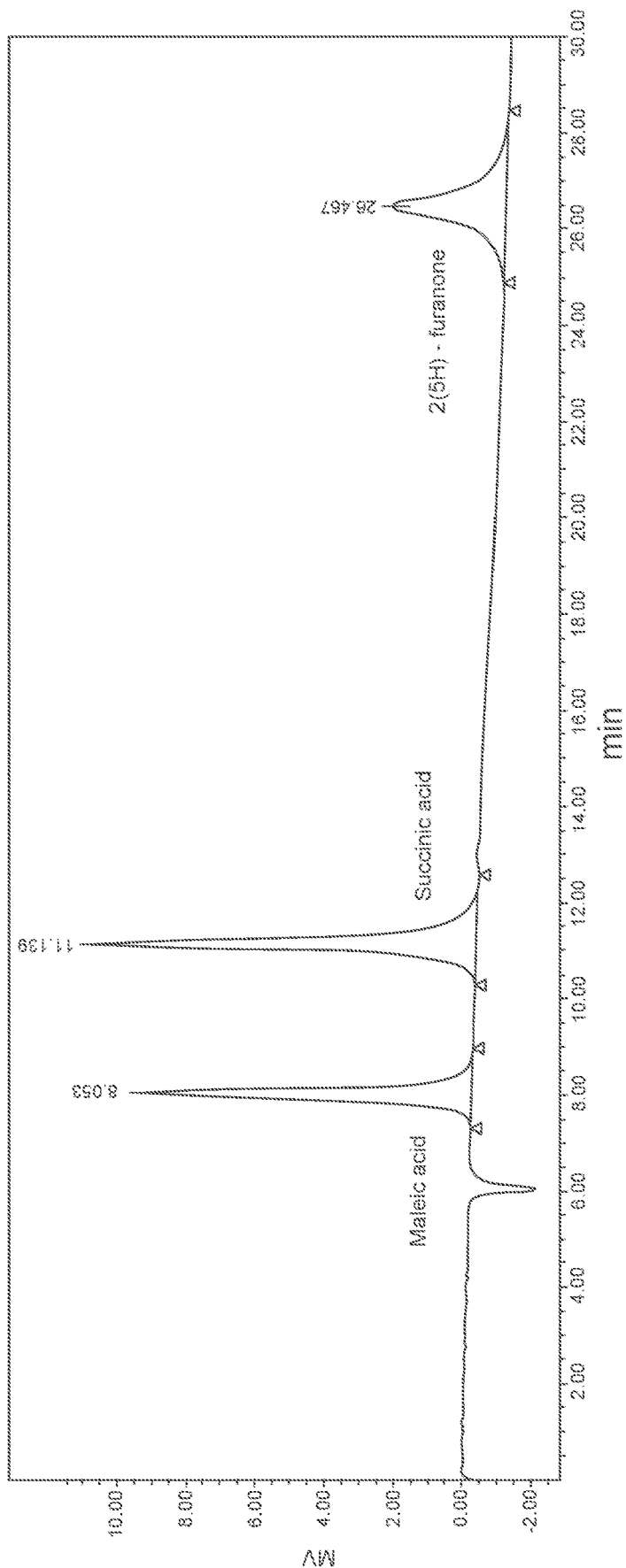
FIG. 2 is an HPLC chromatogram of standard samples of three products of maleic acid, succinic acid, and 2(5H)-furanone.

FIG. 2 shows the retention times of peaks corresponding to standard samples of three products of maleic acid, succinic acid and 2(5H)-furanone. The retention times were 8.053 min, 11.139 min and 26.467 min, respectively. The three products were detected by HPLC.

Embodiment 2

Maleic acid was prepared by catalytic oxidation of furfural with potassium bromide-potassium hydroxide as a catalyst. The preparation method includes the following steps:

1 mmol of furfural, 25 mg of potassium bromide, 50 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 62.35%.

The filtrate was diluted 20 times, and then measured and analyzed by using Waters 515 HPLC (high performance liquid chromatography). The result showed that the conversion rate of furfural in the present embodiment was more than 99%.

Embodiment 3

Maleic acid was prepared by catalytic oxidation of furfural with potassium bromide-sodium hydroxide as a catalyst. The preparation method includes the following steps:

1 mmol of furfural, 25 mg of potassium bromide, 25 mg of sodium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in acetone were sodium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 59.40%.

The filtrate was diluted 20 times, and then measured and analyzed by using Waters 515 HPLC (high performance liquid chromatography). The result showed that the conversion rate of furfural in the present embodiment was more than 99%.

Embodiment 4

Maleic acid was prepared by catalytic oxidation of furfural with potassium bromide-sodium hydroxide as a catalyst. The preparation method includes the following steps:

1 mmol of furfural, 25 mg of potassium bromide, 50 mg of sodium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were sodium hydroxide and potassium bromide. The sodium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 53.65%.

The filtrate was diluted 20 times, and then measured and analyzed by using Waters 515 HPLC (high performance liquid chromatography). The result showed that the conversion rate of furfural in the present embodiment was more than 99%.

Embodiment 5

Maleic acid was prepared by catalytic oxidation of furfural with sodium bromide-potassium hydroxide as a catalyst. The preparation method includes the following steps:

1 mmol of furfural, 25 mg of sodium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in acetone were potassium hydroxide and sodium bromide. The p potassium hydroxide and sodium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 64.44%.

The filtrate was diluted 20 times, and then measured and analyzed by using Waters 515 HPLC (high performance liquid chromatography). The result showed that the conversion rate of furfural in the present embodiment was more than 99%.

Embodiment 6

Maleic acid was prepared by catalytic oxidation of furfural with sodium bromide-sodium hydroxide as a catalyst. The preparation method includes the following steps:

1 mmol of furfural, 25 mg of sodium bromide, 25 mg of sodium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in acetone were sodium hydroxide and sodium bromide. The sodium hydroxide and sodium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 32.21%.

The filtrate was diluted 20 times, and then measured and analyzed by using Waters 515 HPLC (high performance liquid chromatography). The result showed that the conversion rate of furfural in the present embodiment was more than 99%.

Embodiment 7

Maleic acid was prepared by catalytic oxidation of furfural with potassium bromide as a catalyst. The preparation method includes the following steps:

1 mmol of furfural, 25 mg of potassium bromide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the component insoluble in acetone was potassium bromide. The potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 31.65%.

The filtrate was diluted 20 times, and then measured and analyzed by using Waters 515 HPLC (high performance liquid chromatography). The result showed that the conversion rate of furfural in the present embodiment was more than 99%.

Embodiment 8

Maleic acid was prepared by catalytic oxidation of furfural with potassium chloride as a catalyst. The preparation method includes the following steps:

1 mmol of furfural, 25 mg of potassium chloride, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the component insoluble in the acetone was potassium chloride. The potassium chloride can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the filtrate included a main component maleic acid, and some other components including furanone and succinic acid, and the yields were 22.99%, 3.55% and 8.36%, respectively.

The filtrate was diluted 20 times, and then measured and analyzed by using Waters 515 HPLC (high performance liquid chromatography). The result showed that the conversion rate of furfural in the present embodiment was more than 99%.

Embodiment 9

Maleic acid was prepared by catalytic oxidation of furfural with potassium nitrate as a catalyst. The preparation method includes the following steps:

1 mmol of furfural, 25 mg of potassium nitrate, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the component insoluble in the acetone was potassium nitrate. The potassium nitrate can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main components of the filtrate were maleic acid, furanone and succinic acid, and the yields were 12.19%, 25.23% and 27.67%, respectively.

Embodiment 10

Maleic acid was prepared by catalytic oxidation of furfural with potassium hydroxide as a catalyst. The preparation method includes the following steps:

1 mmol of furfural, 50 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the component insoluble in the acetone was potassium hydroxide. The potassium hydroxide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main components of the filtrate were maleic acid, furanone and succinic acid, and the yields were 37.10%, 23.34% and 20.59%, respectively.

The filtrate was diluted 20 times, and then measured and analyzed by using Waters 515 HPLC (high performance liquid chromatography). The result showed that the conversion rate of furfural in the present embodiment was more than 99%.

Embodiment 11

Maleic acid was prepared by catalytic oxidation of furfural with sodium hydroxide as a catalyst. The preparation method includes the following steps:

1 mmol of furfural, 50 mg of sodium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the component insoluble in the acetone was sodium hydroxide. The sodium hydroxide can be reused after recovery. The acetone-extracted filtrate was further evaporated and crystallized to obtain a maleic acid product. The maleic acid product was then dissolved in deionized water for component detection.

Experimental Results:

Components of the above filtrate and yields of the components were detected. The results showed that the main components of the filtrate were maleic acid, furanone and succinic acid, and the yields were 36.14%, 21.51% and 3.30%, respectively.

The filtrate was diluted 20 times, and then measured and analyzed by using Waters 515 HPLC (high performance liquid chromatography). The result showed that the conversion rate of furfural in the present embodiment was more than 99%.

Embodiment 12

Maleic acid was prepared by catalytic oxidation of furfural with potassium bromide and potassium hydroxide as catalysts. The preparation method includes the following steps:

1 mmol of furfural, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 80° C. and stayed for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 55.33%.

The filtrate was diluted 20 times, and then measured and analyzed by using Waters 515 HPLC (high performance liquid chromatography). The result showed that the conversion rate of furfural in the present embodiment was about 85%.

Embodiment 13

Maleic acid was prepared by catalytic oxidation of furfural with potassium bromide and potassium hydroxide as catalysts. The preparation method includes the following steps:

1 mmol of furfural, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 90° C. and stayed for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 64.23%.

The filtrate was diluted 20 times, and then measured and analyzed by using Waters 515 HPLC (high performance liquid chromatography). The result showed that the conversion rate of furfural in the present embodiment was about 95%.

Embodiment 14

Maleic acid was prepared by catalytic oxidation of furfural with potassium bromide and potassium hydroxide as catalysts. The preparation method includes the following steps:

1 mmol of furfural, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 110° C. and stayed for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the main component of the filtrate was maleic acid with a yield of 60.87%.

The filtrate was diluted 20 times, and then measured and analyzed by using Waters 515 HPLC (high performance liquid chromatography). The result showed that the conversion rate of furfural in the present embodiment was about 90%.

Embodiment 15

Maleic acid was prepared by catalytic oxidation of 5-hydroxymethylfurfural with potassium bromide and potassium hydroxide as catalysts. The preparation method includes the following steps:

1 mmol of 5-hydroxymethylfurfural, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and stayed for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the filtrate included a main component succinic acid, and a small amount of maleic acid with yields of 44.94% and 1.33%, respectively.

The filtrate was diluted 20 times, and then measured and analyzed by using Waters 515 HPLC (high performance liquid chromatography). The result showed that the conversion rate of 5-hydroxymethylfurfural in the present embodiment was about 70%.

Embodiment 16

Maleic acid was prepared by catalytic oxidation of 2(5H)-furanone with potassium bromide and potassium hydroxide as catalysts. The preparation method includes the following steps:

1 mmol of 2(5H)-furanonl, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and stayed for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected, and the results showed that the main component of the filtrate was succinic acid with a yield of 19.14%.

The filtrate was diluted 20 times, and then measured and analyzed by using Waters 515 HPLC (high performance liquid chromatography). The result showed that the conversion rate of 2(5H)-furanonl in the present embodiment was about 40%.

Embodiment 17

Maleic acid was prepared by catalytic oxidation of furfural with potassium bromide and potassium hydroxide as catalysts. The preparation method includes the following steps:

1 mmol of furfural, 25 mg of potassium bromide, 25 mg of potassium hydroxide, 4 mL of deionized water were taken and placed in a thick-walled pressure-resistant tube, and 1 mL of a hydrogen peroxide solution was added. Subsequently, a magnetic stirrer was placed in the thick-walled pressure-resistant tube, and then the above solution was placed in an oil bath at a rotation speed of 500 rpm, and the temperature was raised to 100° C. and kept for 3 h. After the reaction is completed, the thick-wall pressure tube was immediately taken out and cooled to room temperature in the air. The reaction liquid was transferred from the thick-walled pressure tube, and the water was removed by rotary evaporation to obtain a solid matter. Then, acetone was used to extract the product, where the components insoluble in the acetone were potassium hydroxide and potassium bromide. The potassium hydroxide and potassium bromide can be reused after recovery. The acetone-extracted filtrate was further evaporated and crystallized to obtain a maleic acid product. The maleic acid product was then dissolved in deionized water for a component detection.

Experimental Results:

Components of the above filtrate and yields of the components were detected. The results showed that the filtrate included a main component maleic acid, and a small amount of succinic acid with yields of 64.76% and 5.70%, respectively.

The filtrate was diluted 20 times, and then measured and analyzed by using Waters 515 HPLC (high performance liquid chromatography). The result showed that the conversion rate of furfural in the present embodiment was more than 99%.

The foregoing descriptions are merely preferred embodiments of the present invention. The protective scope of the present invention is not limited to the above embodiments. Various process solutions with no substantial difference from the conception of the present invention shall fall within the protective scope of the present invention.

What is claimed is:

1. A method for preparing a maleic acid by using a catalyst in a catalytic oxidation of a furfural, comprising: mixing the furfural, the catalyst, an oxidant and a solvent to carry out a reaction to obtain the maleic acid; wherein the catalyst is a bromide-base, the bromide-base is a mixture of a bromide and a base, the bromide is potassium bromide or sodium bromide, and the base is potassium hydroxide or sodium hydroxide.

2. The method according to claim 1, wherein, a mass ratio of the furfural to the bromide-base is (1-1000):100.

3. The method according to claim 1, wherein, the oxidant is at least one selected from the group consisting of hydrogen peroxide, potassium permanganate, potassium chlorate and oxygen.

4. The method according to claim 1, wherein, an amount of the oxidant in a mixed system composed of the furfural, the bromide-base, the oxidant and the solvent is 1-1000 mmol/L.

5. The method according to claim 1, wherein, the solvent is water.

6. The method according to claim 1, wherein, the reaction is carried out at 30-120° C. for a reaction time of 0.5-12 h.

7. The method according to claim 1, wherein, the reaction is carried out under a stirring condition at a stirring rate ranging from 200 rpm to 1000 rpm.

* * * * *